(12) United States Patent
Sakagawa

(10) Patent No.: US 10,628,004 B2
(45) Date of Patent: Apr. 21, 2020

(54) INTERACTIVE CONTROL APPARATUS

(71) Applicant: CANON KABUSHIKI KAISHA, Tokyo (JP)

(72) Inventor: Yukio Sakagawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 122 days.

(21) Appl. No.: 14/011,008

(22) Filed: Aug. 27, 2013

(65) Prior Publication Data

US 2014/0068513 A1 Mar. 6, 2014

(30) Foreign Application Priority Data

Aug. 30, 2012 (JP) ................................ 2012-190001

(51) Int. Cl.
*G06F 3/0484* (2013.01)
*A61B 3/10* (2006.01)
*A61B 3/00* (2006.01)

(52) U.S. Cl.
CPC ........ *G06F 3/04842* (2013.01); *A61B 3/0033* (2013.01); *A61B 3/0075* (2013.01); *A61B 3/102* (2013.01)

(58) Field of Classification Search
None
See application file for complete search history.

(56) References Cited

U.S. PATENT DOCUMENTS

| 2005/0225723 | A1* | 10/2005 | Pilu ........................ A61B 3/113 351/209 |
| 2006/0288848 | A1* | 12/2006 | Gould .................... G06Q 10/08 84/615 |
| 2007/0030528 | A1* | 2/2007 | Quaeler .................. G06F 16/33 358/453 |
| 2007/0083098 | A1* | 4/2007 | Stern .................. A61B 1/00188 600/407 |
| 2008/0059598 | A1* | 3/2008 | Garibaldi ............ G06F 19/3406 709/208 |
| 2008/0100612 | A1* | 5/2008 | Dastmalchi ........... G06F 19/321 345/418 |
| 2009/0073114 | A1* | 3/2009 | Bay ....................... G06F 3/0482 345/156 |
| 2009/0093798 | A1* | 4/2009 | Charles .................. A61F 9/008 606/4 |
| 2010/0202677 | A1 | 8/2010 | Imamura et al. |
| 2011/0199579 | A1 | 8/2011 | Muto |

(Continued)

FOREIGN PATENT DOCUMENTS

| CN | 101040776 A | 9/2007 |
| CN | 101854845 A | 10/2010 |

(Continued)

*Primary Examiner* — Tuan S Nguyen
(74) *Attorney, Agent, or Firm* — Canon U.S.A., Inc. IP Division

(57) ABSTRACT

An interactive control apparatus for controlling an OCT imaging apparatus instructs, in response to detection of a first instruction signal from a pointer device, a specific action to the OCT imaging apparatus according to selected icon displayed on a display unit, and instructs, in response to detection of a second instruction signal from the pointer device, a specific action to the OCT imaging apparatus according to a preparation status of the OCT imaging apparatus when the second instruction signal is detected.

19 Claims, 12 Drawing Sheets

(56) References Cited

U.S. PATENT DOCUMENTS

| | | | |
|---|---|---|---|
| 2011/0286003 A1 | 11/2011 | Ono | |
| 2012/0121158 A1* | 5/2012 | Sekine | G01N 21/4795 382/131 |
| 2012/0263432 A1* | 10/2012 | Shore | G11B 27/34 386/230 |

FOREIGN PATENT DOCUMENTS

| | | | |
|---|---|---|---|
| CN | 102046067 A | 5/2011 | |
| CN | 102160775 A | 8/2011 | |
| EP | 1972265 A2 | 9/2008 | |
| JP | 2005-160549 A | 6/2005 | |
| JP | 2009160190 A | 7/2009 | |
| JP | 2010110393 A | 5/2010 | |
| JP | 2010-181172 A | 8/2010 | |
| JP | 2011-229757 A | 11/2011 | |
| WO | 2010/052929 A1 | 5/2010 | |

\* cited by examiner

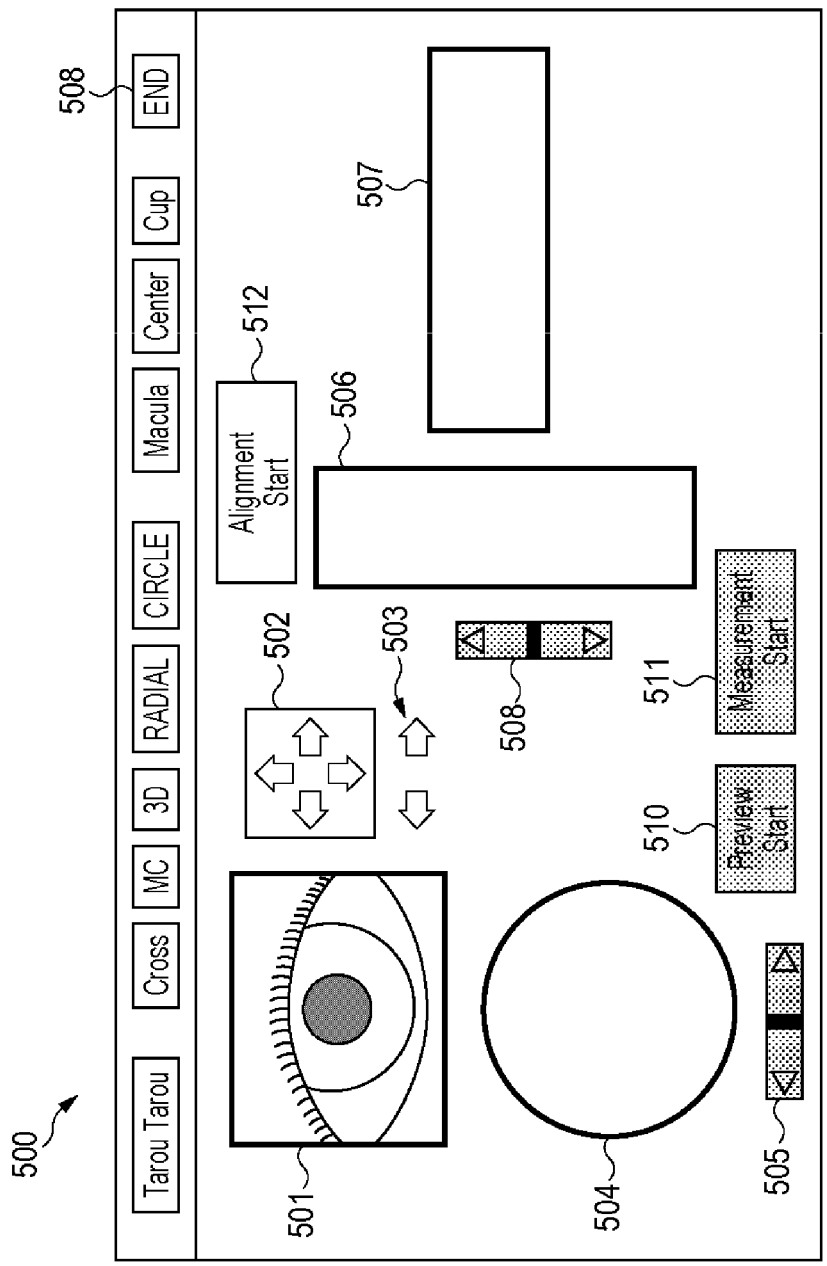

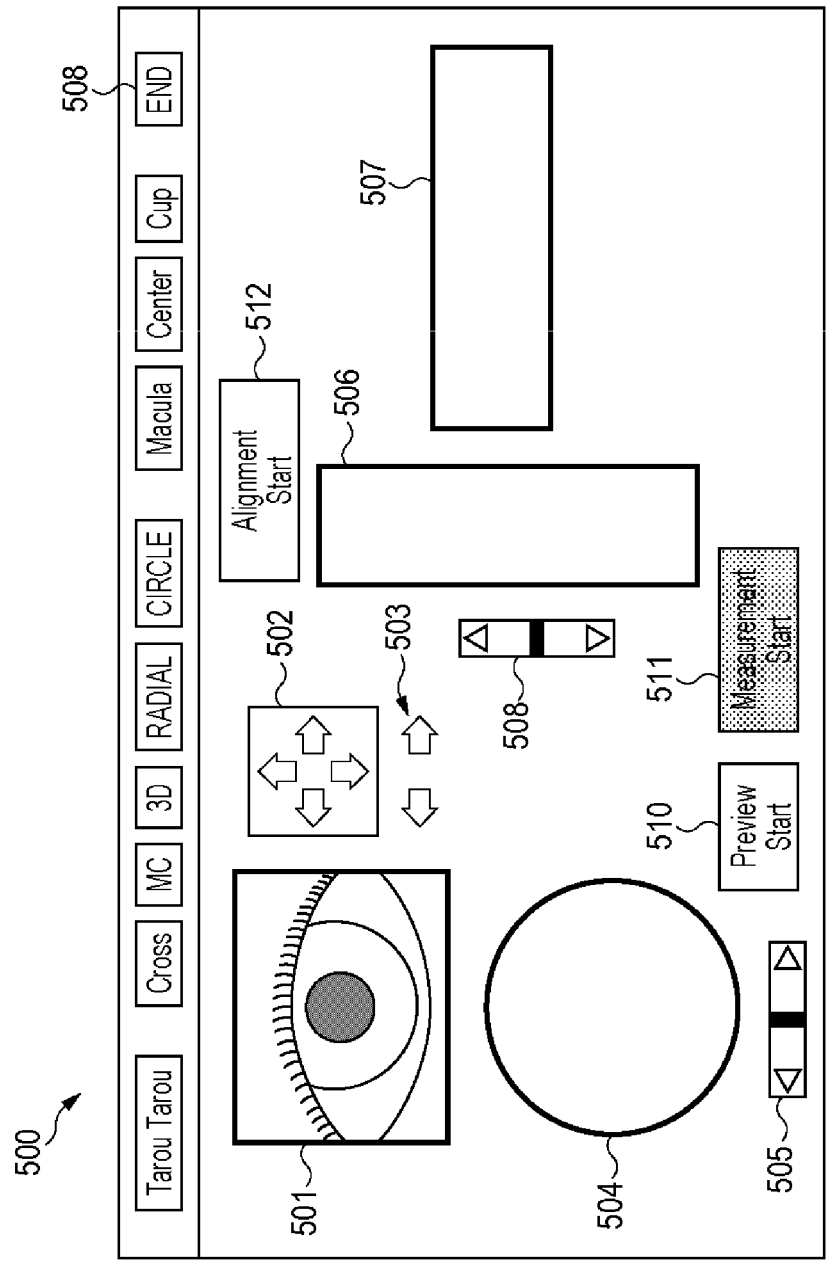

US 10,628,004 B2

INTERACTIVE CONTROL APPARATUS

BACKGROUND

Technical Field

The present disclosure relates to an interactive control apparatus for an imaging apparatus, in particular, for an imaging apparatus performing optical coherence tomography, connecting with a pointer device controlling a virtual pointer on a displayed GUI.

Description of Related Art

In recent years, in medical fields, more specifically in ophthalmic field, imaging apparatuses (hereinafter, also referred to as OCT apparatus) have been used, the apparatuses each picking up tomographic images (hereinafter, also referred to as optical coherence tomographic image) of a test object using optical coherence tomography (OCT) based on interference of low coherence light. The OCT apparatuses utilize light properties, and thereby can obtain tomographic images of high resolution with an order of light wavelength which is micrometer. Generally, the point where the difference between an optical path length of a measurement light beam and that of a reference light beam is zero is called a coherence gate. It is essential to locate a coherence gate at a proper position on a test object's eye to obtain a tomographic image of a high signal to noise (SN) ratio and to display the tomographic image at a proper position on a monitor. Japanese Patent Application Laid-Open No. 2009-160190 discusses an OCT apparatus in which a position of a coherence gate can be specified by moving a cursor displayed on a monitor to facilitate the specification of coherence gate position by user. While a test object's eye such as fundus is measured, the test object's movements, eye blinks, or random slight motions (i.e., involuntary eye movement during visual fixation) are inevitable. The time lag between the adjustment of measurement parameters (focus, coherence gate, etc), and the start of capture of tomograms may result in obtained tomographic images which are not according to the adjusted measurement parameters.

SUMMARY

According to some embodiments of the present invention described below, an interactive control apparatus is provided for an imaging apparatus. The interactive control apparatus is connected with a pointer device configured to output two types of instruction signals. The interactive control apparatus includes a display control unit configured to display, on the display unit, graphical user interface having icons to be selected by a virtual pointer controlled by the pointer device, a detection unit configured to detect a first instruction signal of the pointer device for selecting icons under the virtual pointer, and to detect a second instruction signal of the pointer device, and an acquisition unit configured to acquire a preparation status of the OCT imaging apparatus. The interactive control apparatus also includes a control unit configured to instruct, in response to the detection of the first instruction signal, a specific action to the OCT imaging apparatus according to an icon to be selected by the detected first instruction signal. And the control unit also is also configured to instruct, in response to the detection of the second instruction signal, a specific action to the OCT imaging apparatus according to the preparation status when the second instruction signal detected.

Further features of the present disclosure will become apparent from the following description of exemplary embodiments (with reference to the attached drawings).

BRIEF DESCRIPTION OF THE DRAWINGS

FIGS. 6A and 6B are views of the change of the GUI according to a preparation status, in accordance with an exemplary embodiment.

DESCRIPTION OF THE EMBODIMENTS

Figure 1:
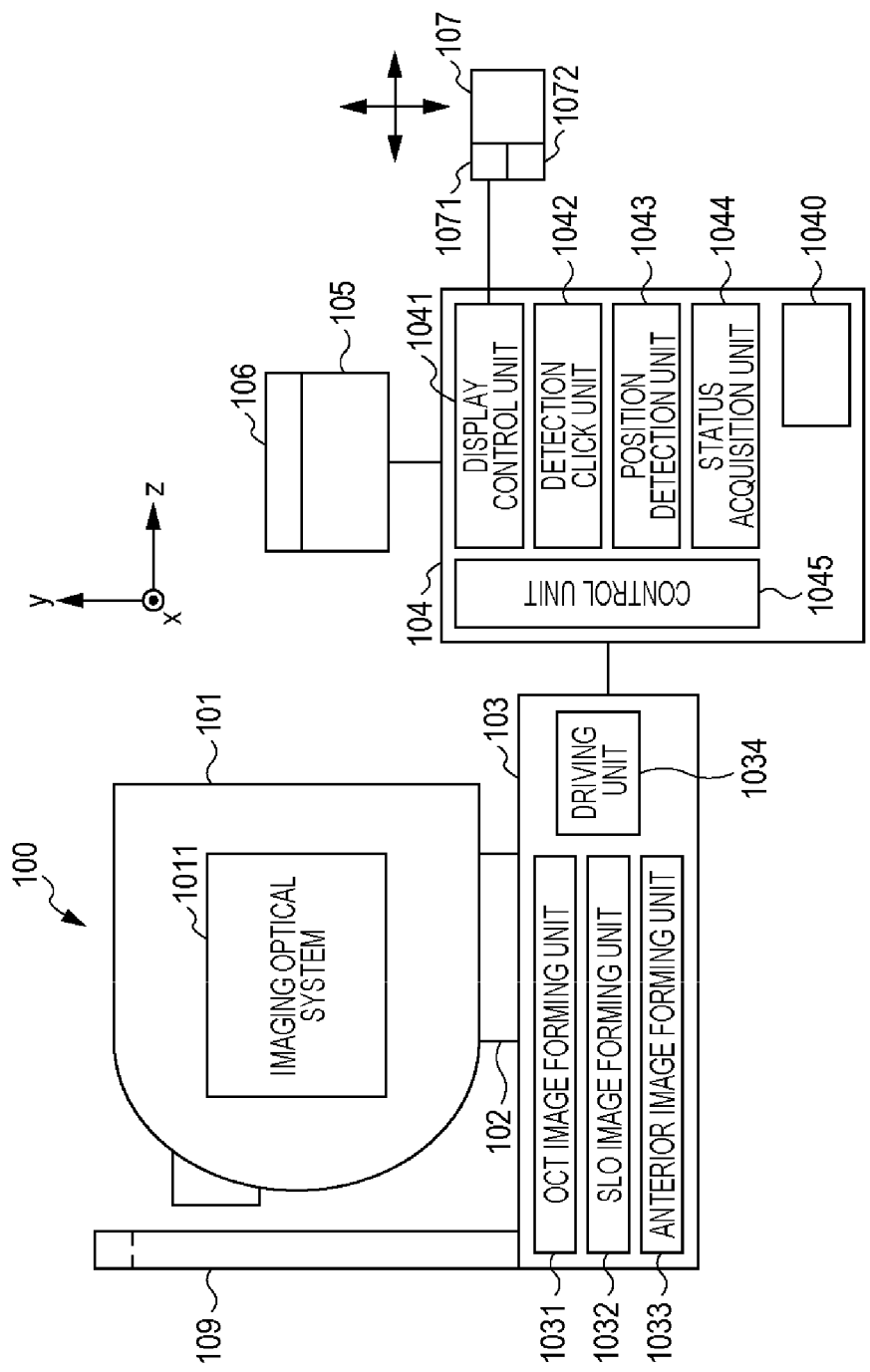
FIG. 1 is a side view of an imaging system according to an exemplary embodiment.

FIG. 1 is a side view of an imaging system according to an exemplary embodiment. In the present embodiment, the imaging system includes an imaging apparatus 100 to obtain an image of a subject using an imaging optical system 1011. Imaging apparatus 100 is connected to an interactive control apparatus 104 for control imaging with a graphical user interface (GUI) displayed on a display unit 105. The interactive control apparatus 104 may be connected to a pointer device 107 which controls a virtual pointer displayed on the display unit 105. The GUI on the display unit may be utilized by the virtual pointer to adjust a plurality of optical elements of the imaging apparatus 100 to prepare to get proper image of the subject. The pointer device 107 obtains an amount of movement or the position of the pointer device. The pointer device also includes two buttons for generating two different types of instruction signals output into the interactive control apparatus.

As shown in FIG. 1, the interactive control apparatus 104 may include a display control unit 1041 configured to display, on the display unit 105, GUI having icons to be selected by the virtual pointer controlled by the pointer device 107, a click detection unit 1042 configured to detect a first instruction signal of the pointer device for selecting icons under the virtual pointer, and to detect a second instruction signal of the pointer device 107.

The interactive control apparatus may also include an status acquisition unit 1044 configured to acquire a preparation status of the imaging apparatus 100, and a control unit 1045 configured to instruct, in response to the detection of the first instruction signal, a specific action to the imaging apparatus 100 according to an icon to be selected by the detected first instruction signal. And the control unit 1045 configured to instruct, in response to the detection of the second instruction signal, a specific action to the imaging apparatus 100 according to the preparation status when the second instruction signal detected.

According to the embodiment the interactive control apparatus 104 provides a plurality of ways of operating for control the imaging apparatus 100.

The specific actions may be for example a start of imaging. If the acquired status indicates that the adjustment for imaging is all completed, the interactive control apparatus 100 instructs start of imaging in response to the detection of the second instruction signal. The control unit 1045 may be configured not to instruct, in response to the detection of the second instruction signal, a specific action to the OCT imaging apparatus according to an icon under the virtual pointer, when the second instruction signal detected. By the second instruction signal, an instruction not based on the position of the virtual pointer but based on the preparation status of the imaging apparatus 100 may be provided to the imaging apparatus. This realizes a quick instruction by using the pointer device without requiring to move the pointer device in order to move the virtual pointer to a specific icon.

In one embodiment, the GUI displayed on the display unit 105 may include an icon for moving a focus lens of the imaging optical system 1011 at a unit of movement per one select for precisely adjusting the focus lens manually by the operator. The icon may be selected by the first instruction signal, corresponding to a first button of the pointer device 107. And the control unit may instruct automatic focus adjustment according to the preparation status in response to the detection of the second instruction signal, corresponding to a second button of the pointer device 107. The GUI may also include an icon for starting automatic focus adjustment, selected by the first instruction signal, corresponding to a first button of the pointer device 107.

According to the embodiment, a way of an operation for automatic adjustment by just clicking the second button, without moving the pointer device 107 is provided. A way of an operation for manual and precise adjustment by moving the pointer device 107 and clicking the first button is provided. A way of an operation for automatic adjustment by moving the pointer device 107 and clicking the second button is also provided.

The instructions output from the control unit 1045 are received by the driving unit 1034 in the imaging apparatus 100. The driving unit 1034 controls motor or the drive mechanism for each of the elements to be adjusted for imaging, such as the focus lens in the imaging optical system 1011.

The imaging apparatus 100 may be an ophthalmic imaging apparatus. As shown in FIG. 1, the imaging system according to the embodiment includes an optical coherence tomography (OCT) imaging apparatus to obtain tomographic image of the fundus or anterior portion of the subject eye. The OCT imaging apparatus of the embodiment includes a scanning laser ophthalmoscope (SLO) forming unit 1032 and an anterior image forming unit 1033 as well as an OCT image forming unit 1031.

The general configuration of the ophthalmic imaging apparatus 100 according to the exemplary embodiment will be described with reference to FIG. 1, which is a side view thereof. An optical head 101 is a measuring optical system for obtaining an image of an anterior eye portion, and a two-dimensional image and a tomographic image of a fundus of the eye.

With a stage unit 102 (also referred to as a moving unit), the optical head 101 is movable with respect to a base unit 103. The stage unit 102 is moved by a motor or the like in X-, Y-, and Z-directions in FIG. 1. The base unit 103 includes a spectroscope which will be described below. The stage unit 102 may be an element to be adjusted for imaging of the subject eye. The GUI displayed on the display unit 105 includes icons for moving the optical head 101 in X, Y, and Z directions, respectively. The GUI also includes an icon for instructing automatic anterior alignment. Automatic anterior alignment is performed to adjust the position of the optical head 101 automatically, by utilizing the anterior image of the subject eye. The control unit 1045 controls the stage unit to so that the anterior image of the subject eye is captured at the specific proper position of the image area. In one embodiment if the icons for X, Y, or Z movement are selected by clicking the first button, the optical head 101 moves according to the selection of icons. If the preparation status of the imaging apparatus 100 is that the adjustment of the stage unit 102 is not completed, and if the second button is clicked, the optical head 101 is adjusted automatically.

An interactive control apparatus 104, which serves as a control unit for the stage unit 102 as well, can construct tomographic images, while controlling the stage unit 102. A hard disk 1040, which also serves as a storage unit for storing information about a subject, stores a program for capturing tomographic images, for example. A display control unit (not illustrated) causes a display unit 105, such as a monitor, to display acquired images and other images. A pointing device (an instruction unit) 107 provides an instruction to the interactive control apparatus 104. More specifically, the pointing device 107 includes a mouse (also referred to as a pointing device). A chinrest 109 is provided to fix a chin and a forehead of a subject.

The embodiments of the Imaging apparatus 100 includes an OCT apparatus, which captures tomographic images of a test object (hereinafter, also referred to as optical coherence tomographic image) by optical coherence tomography (OCT) using interference of a low coherence light beam. The Imaging apparatus 100 is also configured to capture image of the cornea and iris (anterior images) of the subject eye 307. The Imaging apparatus 100 is also configured to capture images of the fundus of the subjective eye. The Imaging apparatus 100 according to the present exemplary embodiment includes an Optical head 101 and a Stage unit 102. The Optical head 101 further includes a Low Coherence Light Source 301, an OCT XY scanner 334, an Reference mirror 332-4, and OCT focus lens 335-5, a line sensor 382, an Anterior image forming unit 1033, anterior image forming unit 1033 and a SLO image forming unit 1032. The Low Coherence Light source 301 generates low coherence light that is split in measurement light beam and reference light beam. The measurement beam goes to the OCT focus lens 335-5 to be focused on the fundus of the subject eye. The measurement beam also goes to the OCT XY scanner 334 to scan the fundus of the subject eye. The OCT XY scanner 334 consists of two scanners (not illustrated), so several B scan tomograms, scanned by the fast scanner, can be captured in different positions defined by the slow scanner. In this way, the measurement light beam is projected to the subject eye, and the return light is combined with the reference light beam after it is reflected by the Reference mirror 332-4.

When the travel distance of the measurement light beam and the reference light beam are the same, the combined light beam contains information about the tomogram of the subject eye. The combined light beam is sent to the line sensor 382, and the combined light beam is then decomposed in several spectrum ranges, which are detected and used to calculate a tomogram of the fundus of the subject eye.

The Anterior image forming unit 1033 is used to capture images of the anterior (cornea and iris) of the subject eye, by the use of an IR light source, an IR camera, and lens to focus the IR camera to the anterior of the eye (cornea).

The SLO image forming unit 1032 is used to capture 2D images of the fundus of the subject eye, by the use of an IR light source, an IR camera and lens that are used to focus the IR camera to the fundus of the eye. It is also obvious for those who have knowledge of previous art that another embodiment of the SLO image forming unit 1032 can be done using SLO (Scanning Laser Ophthalmoscope).

Figure 2:
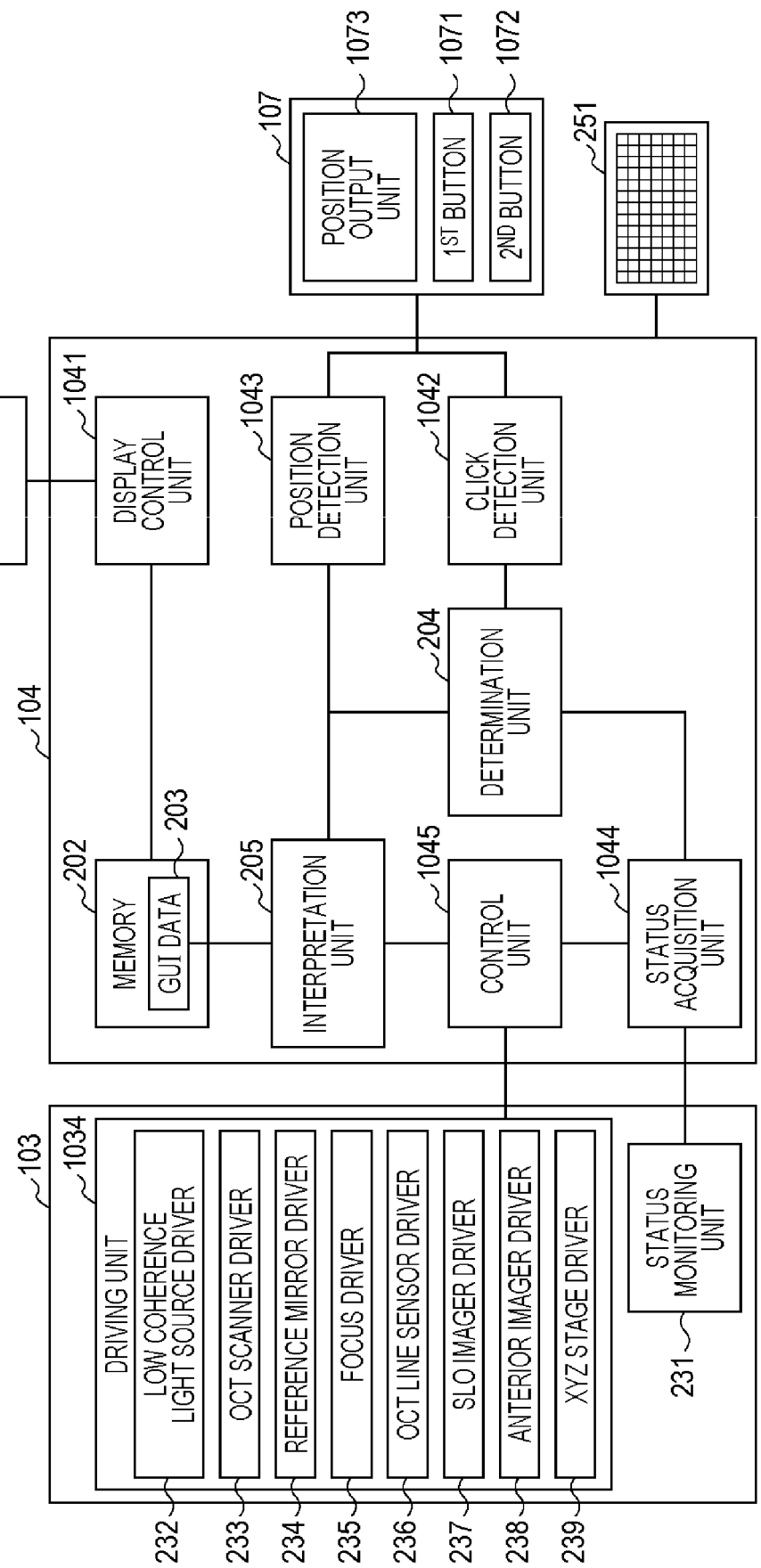
FIG. 2 is a block diagram of the imaging system according to an exemplary embodiment.

Referring to FIG. 2, the interactive control apparatus 104 in accordance with the embodiment of the present invention is described. Interactive control apparatus 104 may be connected to the pointer device 107 and the base unit 103 of the imaging apparatus 100 via a wired or a wireless connection.

The embodiment of the present invention also includes imaging apparatus 100 having the function of the interactive control apparatus as an interactive control unit. The embodiment also includes an apparatus including an interactive control apparatus and the pointer device as one independent apparatus.

The pointer device 107 includes a 1st button 1071, a second button 1072, and a position output unit 1073. The 1st button 1071 and the second button are both clickable by an operator, and the pointer device 107 is movable on a top plane of a table. The pointer device 107 has a laser source and the detector facing with the plane the pointer device is on. A processing unit in the pointer device 107 optically detects the movement of the pointer device 107. The position output unit 1073 outputs the detected movement information as position information to the interactive control apparatus 104. The movement information is output as an amount of movement in an x-direction and a y-direction.

The Pointer device 107 can be any of pointing devices, like mouse, joystick, trackball, etc, or also keyboard or a touch panel device 106 integrally provided on the display unit 106. In the present exemplary embodiment, a mouse with two buttons (Left and Right) and a wheel is used as user input device. In one exemplary embodiment, a press on the right button of the mouse is referred to as right click, and a press on the left button of the mouse is referred as left click. The Pointer device 107 can recognize which button was pressed, and can also recognize one temporary press of the button (click), two temporary press of the button (double click) and send these information to the Display control unit 1041. Pointer device 107 can also recognize when the wheel is rotated, and it also informs to the Display control unit 1041 of how much the wheel was rotated (in pulses). Pointer device 107 can also recognize when the mouse is moved, and it also informs the Display control unit 1041 of when and how much the mouse was moved.

The embodiment of the pointer device 107 includes a mouse device with one button which outputs a first instruction signal by a single click, and which outputs a second instruction signal by a double-click. The embodiment of the pointer device 107 also includes a pointer device with a track ball, which may be rotated by a finger of an operator. The rotation of the track ball may be detected by a rotary encoder, which functions as a position output unit 1073. The embodiment of the pointer device also includes a keyboard 251 with four buttons for moving the virtual pointer by a unit amount towards four respective directions, and two buttons for generating a first instruction signal and a second instruction signal.

The first and second instruction signal and movement information are input into the interactive control apparatus 100 via an interface unit to the pointer device 107. The interface unit may be a USB, PS/2, Bluetooth or other wired or wireless interface. A processing unit determines type of the information and raises an event for each type.

The click detection unit 1042 monitors and detects an event indicating that the first or the instruction signal is output from the pointer device 107, corresponding to the click of the first button 1071 or the second button 1072. The click detection unit 1042 determines which instruction signal is input, and the sends the result of the determination to the determination unit 204.

The position detection unit 1043 monitors and detects an event indicating that the movement information as position information for the virtual pointer is output from the pointer device 107, corresponding to a movement of the pointer device 107. The position detection unit 1043 updates the position of the current position of the virtual pointer on a display screen of the display unit 105, based on a current position information stored in the memory 202, and movement information from the pointer device 107.

The determination unit 204 determines information to utilize for generating signals for controlling the imaging apparatus 100. In a case that the first instruction signal is detected, the determination unit 204 determines that the position information and a GUI data are utilized to generate a control signal for imaging apparatus 100. In another case that the second instruction signal is detected, the determination unit 204 determines that the preparation status is utilized to generate the control signal.

The interpretation unit 205 determines which icon or GUI button is under the virtual pointer. The interpretation unit 205 obtains GUI data, including the position of the icons, images, or buttons configuring the GUI. The interpretation unit 205 also obtains updated position data of the virtual pointer. The interpretation unit 205 determines an icon, an image or a button under the virtual pointer on the GUI displayed on the display unit 105.

The status acquisition unit 1044 acquires a preparation status from a status monitoring unit 231, via another interface unit, for example a universal Serial Bus (USB) port. The status monitoring unit 231 monitors the imaging apparatus 100, updates the current preparation status and stores the preparation status in a memory. The preparation status indicates that the adjustment of each of the elements of the imaging apparatus 100 is completed. For OCT imaging apparatus, the elements includes a low coherence light source to emit OCT, SLO, and anterior imaging light scanning the subject eye, OCT scanner driver to scan the subject eye by the imaging light, a reference mirror for adjusting the optical path length (coherence gate), a focus lens for OCT and SLO imaging light to focus on the subject eye, OCT line sensor to detect the interfering light, an SLO imager to detect a reflection light of the SLO imaging light, an anterior imager to detect a reflection light of the anterior imaging light, the stage unit 102 to align the subject eye and the optical head 101.

For OCT imaging apparatus of the embodiment, each of the element may be adjusted in a predetermined order stored in a memory. In one embodiment, at first adjustment of the stage unit 102 may be performed for the alignment of the subject eye and the optical head 101 (anterior alignment), utilizing an anterior image from the anterior imager. Next, the SLO focus lens adjustment may be performed. SLO imaging is also started at this state by starting the drive of the SLO imager. Next, the OCT focus lens adjustment may be performed. The OCT focus lens position can corresponds to the SLO focus lens position with a look-up table stored in a memory.

OCT imaging (OCT preview) is also started at this stage by starting the drive of the OCT scanner and the OCT imager. Next position of the reference mirror may be adjusted for proper coherence gate position. Since the OCT focus lens is properly positioned, if the reference mirror is adjusted properly, the OCT images of the subject eye will be acquired properly.

Then the all of the elements are adjusted, and the OCT imaging apparatus is prepared for imaging of the subject eye (measurement). When the each of the element is adjust completely, the status monitoring unit 231 updates the preparation status and stores the status in a memory as a current status. The control unit 1045 generates control signals for instructing the adjustment of the elements in the imaging apparatus 100, based on the information determined in the determination unit 204. The control signals are output to the driving unit 1034, via a USB port.

The control unit 1045 instructs adjustment of at least one element, of which adjustment is not completed, based on the acquired preparation status, in response to an instruction signal of the pointer device 107. For example, at the state the anterior alignment is not completed, the control unit 1045 instructs start of the anterior alignment, in response to the click of the second button 1072. At the state the second button 1072 acts as a switch for triggering the automatic anterior alignment.

Automatic anterior alignment may be performed based on the pupil location in the anterior image. The XYZ stage moves the optical head 101 in XY direction in order to adjust the location to the center of the image, and moves the optical head 101 in Z direction in order to adjust the size of the pupil to the specific size.

At the state the OCT preview is not started, the control unit 1045 instructs start of the SLO and SLO focus adjustment, start of the coherence gate adjustment and the start of the OCT imaging, in response to the click of the second button. At the state the second button 1072 acts as a switch for triggering the automatic focus adjustment and automatic coherence gate adjustment. Automatic SLO focus adjustment may be performed based on the pixel values or on the contrast of the SLO image. Once the SLO focus lens is adjusted, the CPU of the OCT imaging apparatus reads a look-up-table indicating the relationship between the SLO focus lens position and the OCT focus lens position. Then the OCT focus lens position is adjusted.

And at the state the adjustment of the coherence gate is completed, which means the completion of the adjustment for the imaging of the subjects eye, the control unit 1045 instructs start of the OCT imaging (measurement), in response to the click of the second button. In other words the control unit 1045 judges whether or not the OCT imaging apparatus is ready for imaging a subject, based on the preparation status. And the control unit 1045 instructs to an OCT imaging apparatus a start of the OCT imaging in a case the control unit 1045 judges that the OCT imaging apparatus is prepared. At the state the second button 1072 acts as a switch for triggering the start of imaging.

According to the embodiment, an interactive control apparatus is provided, the interactive control apparatus instructs to capture an optical coherence tomographic image of a test object and includes the control unit that can start the capture of tomographic images right after the capture parameters are obtained from the user by the pointer device. From another point of view the control unit 1045 assigns at least one of the elements to the second button 1072 according to the preparation status of the imaging apparatus 100. And the control unit 1045 further configured to assign at least one of the elements to the first button 1071 according to the position of the virtual pointer on the graphical user interface.

The control unit 1045 performs a first control to instruct, triggered by the output of a first instruction signal from the pointer device 107, a specific action to the OCT imaging apparatus according to the graphical user interface and the detected position. The control unit 1045 also performs a second control to instruct, triggered by the output of a second instruction signal from the pointer device 107, a specific action to the OCT imaging apparatus according to the preparation status when the second instruction signal detected. The determination unit 204 determines whether to perform the first control or the second control according to the instruction signal output from the pointer device. In this manner the control unit 1045 instructs, in a case a plurality of instruction signals are outputted from the pointer device 107, adjustment of a plurality of elements sequentially in the stored order.

The driving unit 1034 includes drivers for moving or adjusting the position or the state of the elements in the imaging apparatus 100. Each of the drivers applies a voltage to the driving units such as a motor to move or adjust the elements at a specific amount. The driver unit 1034 of the OCT imaging apparatus may include a light source driver 232, an OCT scanner driver 233, a reference mirror driver 234, a focus driver 235, an OCT line sensor driver 236, an SLO imager driver 237, an anterior imager driver 238, and an XYZ stage driver 239.

The display control unit 1041 displays GUI image data stored in the memory 202 on a display screen of the display unit 105 at a predetermined position by GUI position data. The cursor (a virtual pointer) is also displayed on the display screen for select the icons, buttons, or images included in the GUI image data. When the position information is output from the pointer device 107, the display control unit 1041 updates the displaying position of the cursor. The display control unit 1041 may changes the icon of the cursor according to the position on the GUI or the preparation status acquired from the imaging apparatus 100.

(Configurations of Measuring Optical System and Spectroscope)

The configurations of the measuring optical system and a spectroscope in the ophthalmic imaging apparatus 100 according to the present exemplary embodiment will be described below with reference to FIG. 3. The internal configuration of the optical head 101 will be first described. An objective lens 335-1 is placed to face a subject eye 307.

On an optical axis of the objective lens 335-1, a first dichroic mirror 332-1 and a second dichroic mirror 332-2 split light by wavelength band into an optical path 351 of an OCT optical system, an optical path 352 for observation of the fundus and for a fixation lamp, and an optical path 353 for observation of the anterior eye portion. Likewise, a third dichroic mirror 323 splits the light in the optical path 352 by wavelength band into an optical path 354 to a fundus observation charge-coupled device (CCD) 346 and an optical path to a fixation lamp 391. The optical head 101 further includes lenses 335-3 and 335-4. The lens 335-3 is driven by a motor (not illustrated) to adjust focusing for the fixation lamp.

The CCD 346 has sensitivity to the wavelength of illumination light (not illustrated) provided for observation of the fundus, specifically, a wavelength of about 780 nm. The fixation lamp 391 produces visible light to facilitate fixation of the subject eye 307. The optical system for observation of the fundus may include an optical system, such as a scanning laser ophthalmoscope (SLO), for example. In the optical path 353, a lens 335-2 and an anterior eye observation infrared CCD 371 are provided. The CCD 371 has sensitivity to the wavelength of illumination light (not illustrated) provided for observation of the anterior eye portion, specifically, a wavelength of about 970 nm. Further, in the optical path 353, an image splitting prism (not illustrated) is provided, enabling the distance from the optical head 101 to the subject eye 307 in the Z-direction to be detected as split images obtained in an anterior eye observation image.

The optical path 351 forms the OCT optical system as described previously and is used to acquire tomographic images of the fundus of the subject eye 307. More specifically, the optical path 351 is used to obtain an interference signal for forming a tomographic image. An OCT XY scanner 334 scans the fundus with a light beam. The OCT XY scanner 334, illustrated as a mirror, performs scanning in the two axial directions X and Y. The optical head 101 further includes OCT focus lenses 335-5 and lens 335-6. The OCT focus lens 335-5 is driven by a motor (not illustrated) to perform a focus adjustment for focusing a light beam from a low coherent light source 301 emitted from a fiber 331-2 onto the fundus of the subject eye 307. The fiber 331-2 is connected to an optical coupler 331. Concurrently, due to the focus adjustment, light from the fundus of the subject eye 307 forms a spot image and is incident on an edge of the fiber 331-2.

The configurations of the optical path from the low coherent light source 301, a reference optical system, and a spectroscope will be described below. The low coherent light source 301, a reference mirror 332-4, a dispersion compensation glass 315, the optical coupler 331, single-mode optical fibers 131-1 to 331-4, which are connected to the optical coupler 331 as an integral part thereof, a lens 335-7, and a spectroscope 380 form a Michelson interferometer.

A light beam emitted from the low coherent light source 301 travels through the optical fiber 331-1 and the optical coupler 331 in which the light beam is split into a measuring beam to the optical fiber 331-2 and a reference beam to the optical fiber 331-3. The measuring beam travels through the optical path of the above-described OCT optical system to illuminate the fundus of the subject eye 307, which is an object to be observed. The measuring beam is reflected and scattered by the retina, and thus travels to the optical coupler 331 through the same optical path.

The reference beam passes through the optical fiber 331-3, the lens 335-7, and the dispersion compensation glass 315 to reach the reference mirror 332-4 for reflection. The dispersion compensation glass 315 is inserted to compensate for dispersion of the measuring beam and the reference beam. The reference beam returns through the same optical path to the optical coupler 331. The optical coupler 331 combines the measuring beam and the reference beam into interference light (also referred to as combined light). When the measuring beam and the reference beam have substantially the same optical path length, interference occurs. The reference mirror 332-4 is held by a motor and a drive mechanism (not illustrated) so as to be adjustable in the direction of the optical axis. Thus, the optical path length of the reference beam can be adjusted to be equal to the optical path length of the measuring beam that varies depending on the subject eye 307. The interference light is guided to the spectroscope 380 via the optical fiber 331-4.

A polarization adjusting unit 339-1 for the measuring beam is provided in the optical fiber 331-2. A polarization adjusting unit 339-2 for the reference beam is provided in the optical fiber 331-3. The polarization adjusting units 339-1 and 339-2 include some portions of the optical fibers 331-2 and 331-3 each routed in the shape of a loop. The polarization states of the measuring beam and the reference beam can be adjusted to each other by turning these loop-shaped portions with the longitudinal direction of each fiber being the center, and thereby twisting the fibers 331-2 and 331-3. In the apparatus according to the present exemplary embodiment, the polarization states of the measuring beam and the reference beam are adjusted and fixed in advance. The spectroscope 380 includes lenses 335-8 and 335-9, a diffraction grating 381, and a line sensor 382. The interference light emitted from the optical fiber 331-4 is collimated into approximately parallel light by the lens 335-8. The parallel light is then dispersed by the diffraction grating 381 to form an image on the line sensor 382 through the lens 335-3.

The low coherent light source 301 and its periphery will be described in more detail below. The low coherent light source 301 is a super luminescent diode (SLD), a typical low-coherence light source. The low coherent light source 301 has a center wavelength of 855 nm and a wavelength bandwidth of about 100 nm. The bandwidth, which affects the resolution of an acquired tomographic image in the direction of the optical axis, is an important parameter. In the present exemplary embodiment, the type of low coherent light source employed is an SLD. However, any other type of low coherent light source, for example, an amplified spontaneous emission (ASE) device, may also be used so long as low-coherence light can be emitted. Since a human eye is an object to be measured, near infrared light is suitable as the center wavelength. The center wavelength, which affects the resolution of an acquired tomographic image in the transverse direction, is preferably a short wavelength. For those two reasons, the center wavelength is set to 855 nm.

In the present exemplary embodiment, a Michelson interferometer is employed. However, a Mach-Zehnder interferometer may also be used. When a difference in the amount of light between the measuring beam and the reference beam is relatively small, a Michelson interferometer, in which a single splitting and combining unit is provided, is preferable to a Mach-Zehnder interferometer, in which a splitting unit and a combining unit are provided separately.

(Scanning Laser Ophthalmoscope: SLO)

Figure 3:
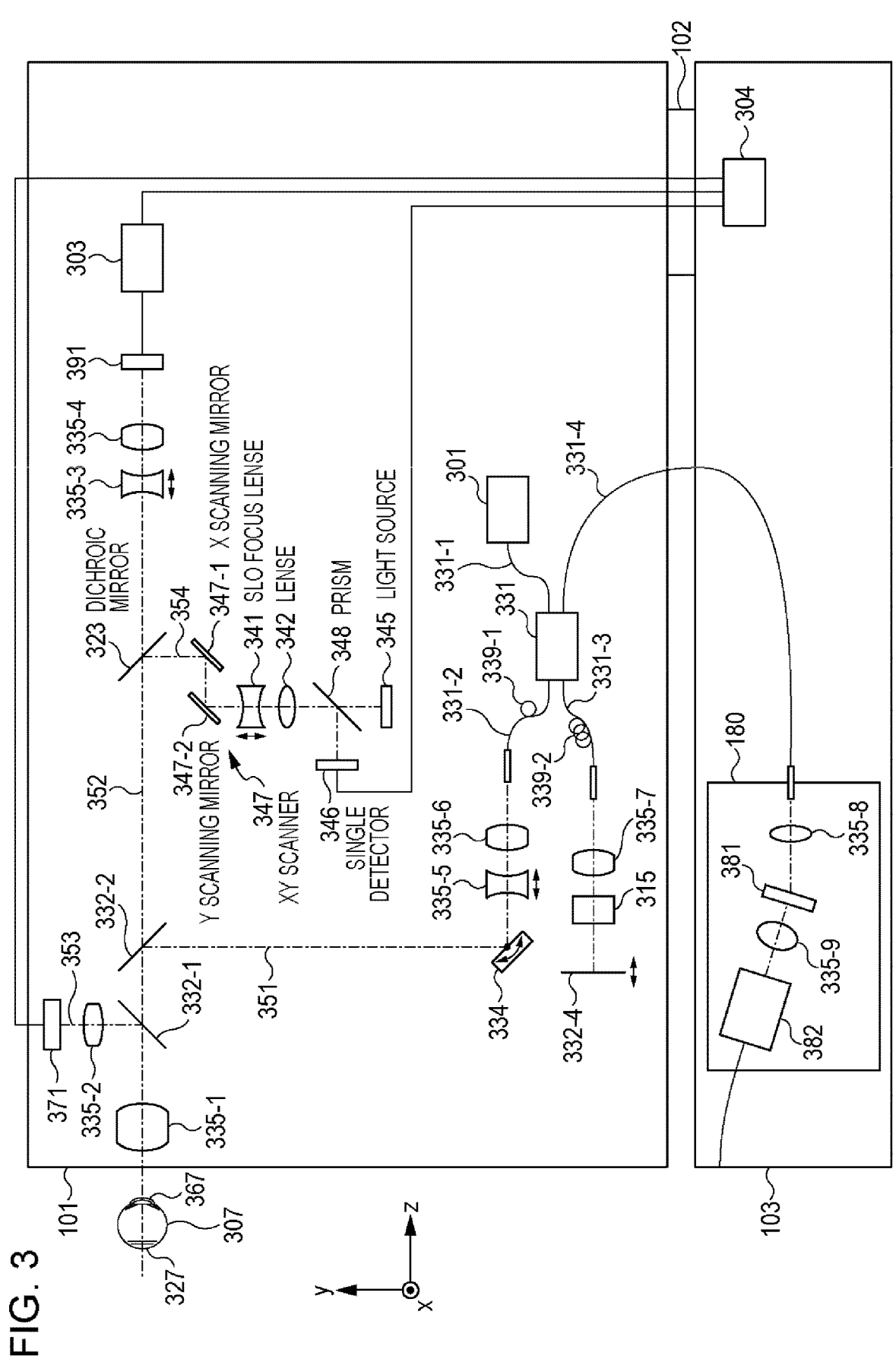
FIG. 3 is a view of the imaging optical system in the imaging apparatus according to an exemplary embodiment.

Referring to FIG. 3, a schematic overall configuration of an optical system of the SLO according to present embodiment is also described. An illumination beam emitted from a low coherent light source 345 is deflected by a prism 348 and scanned by an SLO XY scanner 347. The SLO XY scanner 347 is actually composed of two mirrors, an X scanning mirror 347-1 and a Y scanning mirror 347-2, disposed in proximity to each other. Therefore, the SLO XY scanner 347 may raster scan the fundus in a direction perpendicular to an optical axis.

The focus position of the illumination beam may be adjusted by a SLO focus lens 341 and a lens 342. The SLO focus lens 342 may be driven by a motor to adjust focusing. After entering the eye to be inspected, the illumination beam is reflected or scattered by the fundus and then returned as a return beam. The return beam enters the prism 348 again, and a beam transmitted therethrough enters a sensor 346. The sensor 346 converts a light intensity of the return beam at each measurement point of the fundus to a voltage, and feeds a signal indicating the voltage to the memory control and signal processing portion 304. The memory control and signal processing portion 304 uses the fed signal to generate a fundus image, which is a two-dimensional image. A part of the memory control and signal processing portion 304 cooperates with the optical system and the sensor 346 described above to constitute a fundus imaging unit for taking a fundus image in this embodiment. Further, the memory control and signal processing portion 304 extracts, from the two-dimensional image, a region of a predetermined shape and size that includes a feature point having a feature such as a crossing or branching area of blood vessels in the fundus as a template. Therefore, the template is image data of the region including the feature point.

Here, the memory control and signal processing portion 304 has a function constituting a template extracting unit for executing the above-mentioned extraction of the template from the fundus image. Template matching is executed on a newly generated two-dimensional image by using the extracted template, to thereby calculate a moving amount of the eye to be inspected. Further, the memory control and signal processing portion 304 executes tracking depending on the calculated moving amount.

The memory control and signal processing portion 304 also includes a keyboard or mouse (not shown) and supports external input. Further, the memory control and signal processing portion 304 controls start and end of the fundus imaging. The memory control and signal processing portion 304 also includes a monitor (not shown) and may display the fundus image and specific information of the eye to be inspected. This allows an operator to observe the fundus in an image. Further, the template extracted by the memory control and signal processing portion 304 is recorded in a memory portion with the input specific information of the eye to be inspected. Specifically, the extracted template and the specific information identifying the eye to be inspected, of which the fundus image from which the template is extracted is taken, are recorded in association with each other in the memory portion under the memory control of the memory control and signal processing portion 304.

Figure 4C:
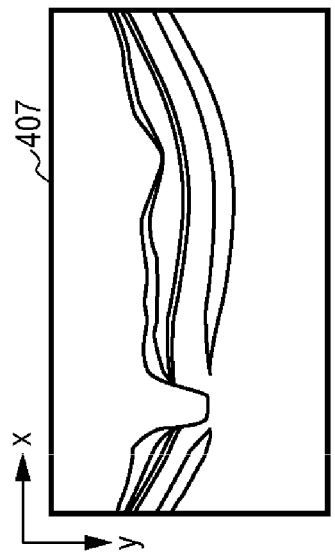
FIGS. 4A, 4B and 4C are examples of images captured by OCT imaging apparatus, according to an exemplary embodiment.
Figure 4B:
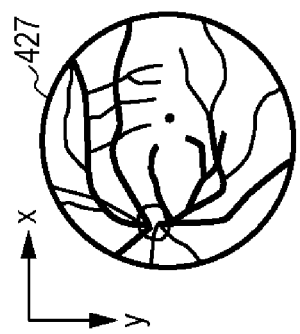
Figure 4A:
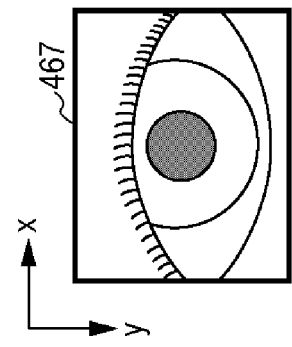

FIGS. 4A, 4B and 4C are views of an eye anterior transaxial image 467, a transaxial fundus image 427 and a longitudinal tomogram image 407 of the retina that are all captured by the OCT imaging apparatus. The anterior image 467 is for alignment of the subject eye and the imaging optical system 1011 before the measurement with OCT. The fundus image 427 is for determining a scan line position of OCT before the measurement, and for diagnosis after the measurement. The tomogram image 407 is confirming the scan line position before the measurement and for diagnosis of the fundus after the measurement.

The images 407, 427 and 467 are displayed on the display unit 105 as the GUI. The images 407, 427 and 467 are transmitted from the imaging apparatus 100 to the interactive control apparatus, via IEEE 1394, what is called a firewire, or a camera-link interface. In one embodiment the connecting wire may be doubled for widening the communication bandwidth, which reduces the time gap between the time of the imaging and the time of the display of the images.

Figure 5:
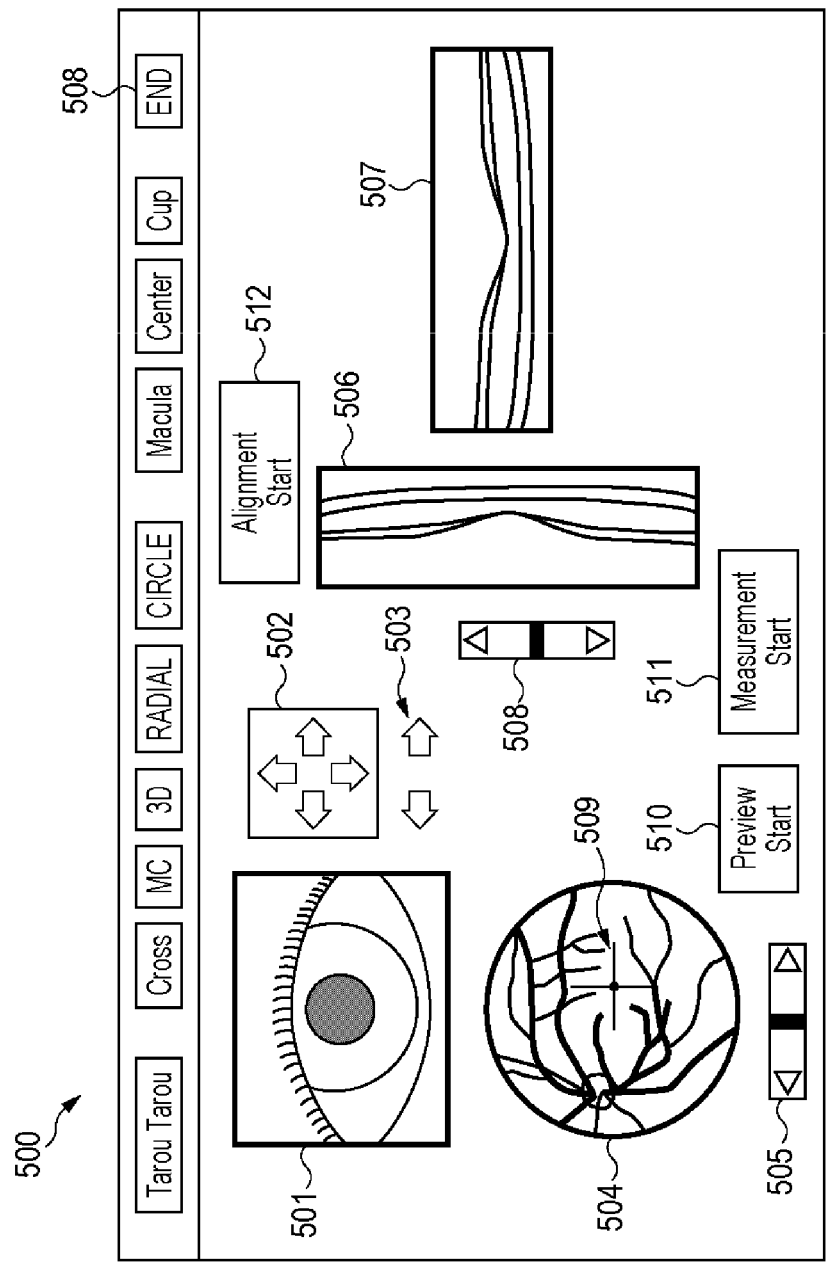
FIG. 5 is a view of the GUI displayed in the Display Unit, according to a first exemplary embodiment.

Referring to FIG. 5, The GUI displayed on the display unit 105 and the interaction with an operator the interactive control apparatus 104 are described. In the present exemplary embodiment, the Display control unit 1041 is configured to control the display of GUI and captured images in the Display unit 105, and also configured to process the user instruction. The Display control unit 1041 also includes a Capture State Controller (not illustrated) configured to control the Capture State. The Display control unit 1041 also displays a mouse cursor in the Display unit 105 based on the instructions obtained from the Pointer device 107. The Display control unit 1041 also recognizes the coordinates on the Display unit 105, and it can identify in which region of the Display unit 105 the cursor is. Also, when the Anterior Image is displayed in the Display unit 105, the Display control unit 1041 recognizes the position of the cursor inside the Anterior Image. Similarly, the Display control unit 1041 recognizes when the cursor is over the fundus image, or a tomogram image, or one Icon of the GUI.

In the present exemplary embodiment, a mouse is used as Pointer device 107 and Display control unit 1041 moves and recognizes the position of the cursor on the Display unit 105 according to the amount of movement of the mouse obtained by the Pointer device 107. Accordingly, the Display control unit 1041 recognizes the position of the cursor when the pointer device 107 recognizes a left click on the button, or the rotation of the wheel of the mouse.

The Display control unit 1041 includes a Capture State Machine which controls the present state of the Control Unit 1045. In the present exemplary embodiment, the states are Anterior Alignment State, OCT Preview State and OCT Measurement State. The state changes according to the instructions input from the user.

Every time the Capture State changes, Display control unit 1041 sends the updated Capture State to the Control Unit 1045. According to the user input obtained by pointer device 107, Display control unit 1041 sends capture information to Control Unit 1045, information that are necessary to generate capture parameters. The capture parameters can be OCT scan position, focus adjustment, XYZ stage position, etc.

The Control Unit 1045 is configured to control the Imaging apparatus 100. The Control Unit 1045 gives instructions and capture parameters necessary for the capture of OCT tomograms, anterior image, and fundus image by the Imaging apparatus 100. In other works, the Capture Control Unit gives instructions about optical head position, OCT scanning position and focusing, coherence gate positions, and others. The optical head position refers to a relative position between the optical head and the subject eye in such that the sampling bean of OCT can scan the fundus of the subject eye. OCT scanning position refers to the position of the fundus of the subject where the OCT is going to be scanned. OCT focusing refers to the focus of the OCT, such that the OCT tomogram image has enough contrast. The coherence gate position refers to a position where the difference of optical path of the reference light beam and sample light beam is zero.

The Control Unit 1045 can be in one of the following Capture State Anterior Alignment State, OCT Preview State or OCT Measurement State. The Display unit 105 is configured to show to the user (not illustrated), the GUI and images (anterior image, fundus image and tomogram image) obtained from the OCT image forming unit 1031. The layout of the GUI and position of the images shown by the Display unit 105 are controlled by the Display control unit 1041.

The following processing process is performed by the imaging apparatus according to the present exemplary embodiment, to perform Anterior Alignment. Anterior Alignment is the adjustment of the position of optical head 102 by controlling Stage unit 102 to allow the OCT measurement beam to be projected onto the fundus of the eye. The processing flow is described with reference to FIG. 5. FIG. 5 shows an example GUI 500 to be displayed to the user by the Display unit 105.

The OCT image forming unit 1031 acquires an anterior image of the subject eye from the OCT Capture Unit, and it sends the anterior image to the Display control unit 1041 that shows the anterior image 501 to the user (not illustrated) by displaying the image in the Display unit 105. The Display control unit 1041 also displays XY stage icons 502 and Z stage icon 503 in the Display unit 105, these icons being used to indicate control movements of the Stage unit 102. The Pointer device 107 detects movements of the mouse, and also detects if left or right button was pressed (clicked). Display control unit 1041 then decides if the user moved the cursor to over the icon, and left clicked it. The Up/Down arrows of the XY stage icons 502 are for up/down movements of the Y stage. The Left/Right arrows of the XY stage icons 502 are for left/right movements of the X stage. The Left/Right arrows of Z stage icon 503 are for backward/forward movements of the Z stage.

If the Display control unit 1041 detected that the user left clicked the icon, then Display control unit 1041 will send a corresponding command to Control Unit 1045, to move XYZ stage. Instead of use of icon, the user can also control the movement of Stage unit 102 by left clicking on the anterior image, or using the wheel when the cursor is over the anterior image. If the user left clicks on the anterior image, Display control unit 1041 calculates the amount of movement to send to XYZ stage, to bring the clicked position to the center of the anterior image.

In one embodiment, the automatic anterior-alignment may be started in response to the select of the alignment start icon 512 by analyzing the pupil of the subject eye in the anterior image 501.

The following flow is performed by the imaging apparatus according to the present exemplary embodiment, to adjust the focus of the fundus image and OCT tomogram image. The processing flow is described with reference to FIG. 5.

The OCT image forming unit 1031 acquires a fundus image of the subject eye from the OCT Capture Unit, and it sends the fundus image to the Display control unit 1041 that shows the fundus image 504 to the user (not illustrated) by displaying the image in the Display unit 105. The Display control unit 1041 also displays focus icon 505 in the Display unit 105, these icons being used to indicate control movements of the focus for fundus camera. The Pointer device 107 detects movements of the mouse, and Display control unit 1041 decides if the user moved the cursor to over the icon, and left clicked it. The Left/Right arrows of focus icon 505 are to move fundus focus to a closer or farther point. If the Display control unit 1041 detected that the user left clicked the icon, then Display control unit 1041 will send a corresponding command to Control Unit 1045, to move focus of fundus camera. The user can observe the fundus image 504 to decide if the image is in focus, and change the focus position by left clicking the focus icon 505 if necessary. Instead of use of icon, the user can also control the movement of fundus camera focus by using the wheel when the cursor is over the anterior image. After each adjustment done by the user, the value of the fundus camera focus is also given to the OCT focus lens 335-5, to adjust OCT measurement beam focus to the same point as fundus camera focus.

The following process is performed by the imaging apparatus according to the present exemplary embodiment, to adjust the position of the OCT reference mirror for coherence gate adjustment, and to adjust the scanning position of the OCT tomogram. The processing flow is described with reference to FIG. 5. The OCT image forming unit 1031 acquires an OCT tomogram image of the subject eye from the OCT Capture Unit, and it sends the OCT tomogram image to the Display control unit 1041 that shows a vertical tomogram image 506 and a horizontal tomogram image 507 to the user (not illustrated) by displaying the image in the Display unit 105. The Display control unit 1041 also displays coherence gate (CG) icon 508 in the Display unit 105, these icons being used to indicate control movements of the Reference mirror 332-4. The Pointer device 107 detects movements of the mouse, and Display control unit 1041 decides if the user moved the cursor to over the icon, and left clicked it. The Up/down arrows of CG icon 508 are to move the position of OCT reference mirror so that reference beam optical path can be longer or shorter than the measurement beam optical path.

If the Display control unit 1041 detected that the user left clicked the icon, then Display control unit 1041 will send a corresponding command to Control Unit 1045, to move position of reference mirror. The user can observe the vertical tomogram image 506 and the horizontal tomogram image 507 to decide if the tomogram of the fundus of the subject eye is present in the image, and change the position of the reference mirror by left clicking the CG icon 508 if necessary. Instead of use of icon, the user can also control the movement of reference mirror by using the wheel when the cursor is over the anterior image.

Display control unit 1041 also detects if the user moves the cursor over the OCT scanning position marks 509. If the user left clicks over the OCT scanning position marks 509 and drags it over the fundus image 504, Display control unit 1041 calculates the position final position of the OCT scanning position marks 509 over fundus image 504. Display control unit 1041 then sends these information to Control Unit 1045, which convert information from Display control unit 1041 to control information for the OCT XY scanner 334. OCT XY scanner 334 then moves the OCT scanners to perform the scanning of OCT tomograms on the position of the subject fundus eye, that is according to the position of the OCT scanning position marks 509 over fundus image 504.

The displayed GUI in one embodiment is shown in FIGS. 6A and 6B. In the GUI in FIG. 6A, when the anterior alignment is not completed, the area displaying the fundus image 504 and the tomogram images 506 and 507 may color white, and the icons 505, 508, 510 and 511 may be not enabled by the display control unit 1041. And the anterior image 501, icons 502 and 503, and 512 may be enabled by the display control unit 1041. This makes only the images or icons concerning the anterior alignment enabled, which notifies the operator the preparation status of the OCT imaging apparatus.

As shown in FIG. 6B, when the alignment is completed, the area of the image 504, 506 and 607, and icons 505, 508 and 510, all concerning with the OCT preview imaging, are changed to be enabled. This notifies the operator that the focus of the SLO and OCT imaging light are required for the preview imaging. In this status, the area of the anterior image 501 and icons 502 and 503 may still be enabled, because the relative position of the subject eye and the optical head 101 can be changed and further alignment will be needed for imaging properly, before the start of the measurement with OCT.

Figure 7:
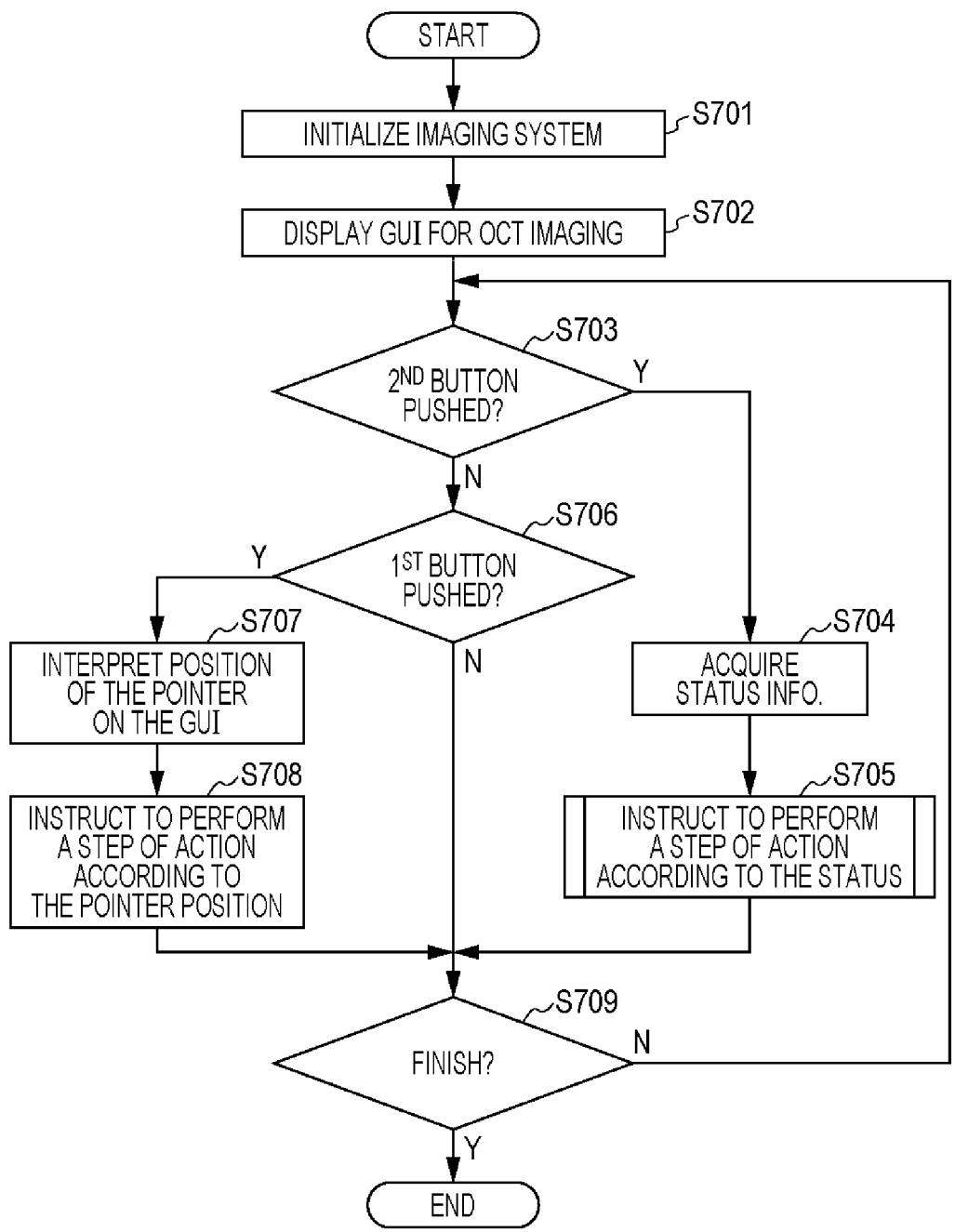
FIG. 7 is a flowchart of an operation of interactive control apparatus according to an exemplary embodiment.

Referring to the flowchart of FIG. 7, the process of the interactive control of the imaging apparatus 100 according to an embodiment is described. In step S701 the imaging system 100 is initialized by each central processing unit (CPU) of the apparatuses. The control unit 1045 initializes Capture State, or preparation status, to Anterior Alignment State. In one embodiment the initialization may be triggered by the push of the power switch of the imaging apparatus 100 or the interactive control apparatus 104. In response to the push of the power switch of one apparatus, triggering signals for the one apparatus and for the other apparatus are generated, and both the apparatus are initialized. This reduces the time for preparation before the start of medical imaging.

In step S702, display control unit 1041 displays the GUI, as shown in FIG. 5 or FIG. 6A. In step S703, the click detection unit 1042 determines whether the click detection unit 1042 detects click of the 2nd button 1072. In step S704, performed in the case the click of the second button 1072 is detected, the determination unit 204 outputs the instruction signal, and the status acquisition unit 1044 acquires the current preparation status information from the imaging apparatus 100. In one embodiment the status acquisition unit 1044 continuously received the preparation status information from the imaging apparatus 100, corresponding to the change of the current preparation status. The preparation status may be stored in the memory 202 and may be displayed by the display control unit 1041, in response to the receipt of the preparation status. This notifies the operator the current status of the preparation status.

In step S705, the control unit 1045 generates signals for instructing to perform a step of action according to the status. Further detail of the process is described below, with reference to FIG. 8. In step S706, the click detection unit 1042 determines whether the click detection unit 1042 detects click of the first button 1071. In one embodiment the order of the process of step S703 and step S706 may be interchangeable. Or the step S703 and the step S706 may be integrated into one step.

In step S707, performed in the case the click of the first button 1071 is detected, the interpretation unit 205 determines an icon or an image under the virtual pointer, based on the current position of the cursor and the GUI data 202, both stored in the memory 203. In step S708, the control unit 1045 instructs to perform a step of action according to the position of the pointer and the GUI data displayed on the display unit 105.

In step S709, CPU of the interactive control unit 104 determines whether a finish signal indicating a finish of imaging for a subject eye is detected. In the case the finish signal is detected, corresponding to a selection of the END icon 508, the process for the imaging of the subject eye is detected. In the case the finish signal is not detected, the process of the step S703 is performed again. In one embodiment, the finish signal, the first and second instruction signal corresponding to the first button 1071 and the second button 1072 may be continuously and parallelly. The order of some of steps may be changed.

Figure 8:
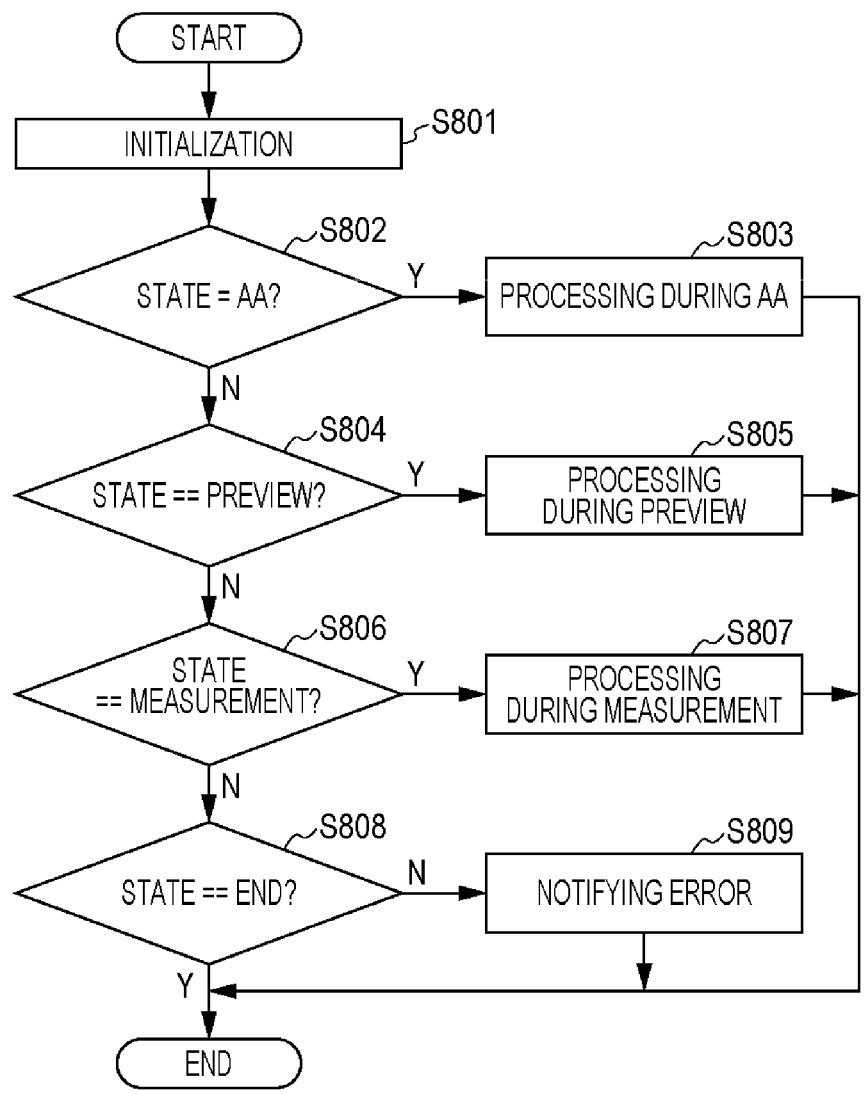
FIG. 8 is a flowchart of a control process of the interactive control apparatus according to an exemplary embodiment.

Referring to flowchart of FIG. 8, the process in the step S705 is described. The following processing flow is performed by the imaging apparatus according to the present exemplary embodiment, to the control the transition of Capture State. The processing flow is described with reference to FIG. 8. FIG. 5 is also used as reference to show an example of the GUI 500 during the execution the processing flow.

In Step S801, the control unit 1045 initializes the process. In Step S802, the control unit 1045 checks if Capture State is in Anterior Alignment State. If Capture State is different than Anterior Alignment State, then processing goes to Step S804. If Capture State is Anterior Alignment State, then processing goes to Step S803. In Step S803, this exemplary embodiment of the Imaging apparatus perform processing done during Anterior Alignment State.

In Anterior Alignment State only Adjustment of position of Optical head 101 by controlling the stage unit 102, as explained previously, is allowed. During Anterior Alignment State, the Control Unit 1045 may not instruct capture fundus image, and also may not capture OCT image. Also, Display control unit 1041 inhibits the adjustment of focus of fundus image, adjustment of reference mirror position and adjustment of scanning position of OCT tomogram, by disabling the icons for the adjustment.

In Step S803, Preview Start icon 510 is enabled, and Measurement Start icon 511 is disabled. If the interpretation unit 205 detects that Preview Start Icon 510 was left clicked, then the control unit 1045 changes Capture State to OCT Preview State. Also in Step S803, if the click detection unit 1042 detects that user has right clicked the mouse when the cursor is over the GUI 500, the control unit 1045 changes Capture State to OCT Preview State.

In Step S804, the control unit 1045 checks if Capture State is in OCT Preview State. If Capture State is different than Preview State, then processing goes to Step S806. If Capture State is OCT Preview State, then processing goes to Step S805. In Step S805, this exemplary embodiment of the Imaging apparatus perform processing done during Preview State. In Preview State, Adjustment of position of Optical head 101 by controlling Stage unit 102, as explained previously, is allowed. During Preview State, the Control Unit 1045 instructs to perform capture of fundus images, and also capture of OCT images. Display control unit 1041 also allows the adjustment of focus of fundus image, adjustment of reference mirror position and adjustment of scanning position of OCT tomogram, by enabling the icon for the adjustment, as previously explained.

In Preview State, Preview Start icon 510 is changed to Preview Stop icon (not illustrated), and Measurement Start icon 511 is enabled. If the interpretation unit 205 detects that Preview Stop icon was left clicked, then the control unit 1045 changes Capture State to Anterior Alignment state. If the interpretation unit 205 detects that Measurement Start icon 511 icon was left clicked, then the control unit 1045 changes Capture State to OCT Measurement state. Also in Step S805, if click detection unit 1042 detects that user has right clicked the mouse when the cursor is over the GUI 500, the control unit 1045 changes Capture State to OCT Measurement State.

In another embodiment of the Imaging apparatus, in Step S805, Display control unit 1045 instructs to perform automatic Anterior Alignment, automatic adjustment of focus of fundus image, and automatic adjustment of reference mirror position. These automatic functions are performed right after the Capture State is changed to OCT Preview State.

Automatic Anterior Alignment may be performed as follows: Display control unit 1041 first obtains anterior image of the subject eye, then perform image processing in the anterior image to recognize the position of the center of the pupil of the subject eye in the anterior image. Then, Display control unit 1041 sends this pupil position information to Control Unit 1045. Control Unit 1045 then calculates the amount of XY stage movement that corresponds to the difference in position of the pupil position and the center of anterior image. Z stage can be adjusted by analyzing the focus condition of the anterior image. Control Unit 1045 then moves Z stage in such a way that anterior image becomes sharp. The calculated amount of XYZ movement is then sent to Stage unit 102 that accordingly moves the position of the Optical head 101.

Automatic focus adjustment of fundus image may be performed as follows: Display control unit 1041 first obtains fundus image of the subject eye, then it performs image processing in this image to calculate the contrast of this image. Then Display control unit 1041 send command to Control Unit 1045 to move the position of focus of SLO image forming unit 1032.

After the movement, Display control unit 1041 obtains another fundus image of the subject eye, and then calculates the contrast of this image. This cycle "Move focus and calculate contrast of fundus image" is done until the contrast value is higher than a predetermined threshold. When this cycle is finished, then the value information of fundus image focus is sent to OCT Focus Mechanism to accordingly set the position of the OCT focus.

Automatic adjustment of OCT Reference Mirror (Coherence Gate) may be performed as follows: Display control unit 1041 first obtains OCT Tomogram image of the subject eye, then it performs image processing in this image to check if image of retina was obtained. Then Display control unit 1041 send command to Control Unit 1045 to move the position of reference mirror of Reference mirror 332-4. After the movement, Display control unit 1041 obtains another OCT Tomogram image of the subject eye, and then checks if image of retina was obtained. This cycle "Move reference mirror and check if retina image was obtained" is done until retina image is obtained.

The Automatic functions are executed in the order of anterior alignment, focus adjustment and reference mirror position adjustment. These Auto functions may also be executed at arbitrary times in step S805, when Display control unit 1041 detects input from the user to perform these auto functions.

In Step S806, the control unit 1045 checks if Capture State is in OCT Measurement State. If Capture State is different than OCT Measurement State, then processing goes to Step S808. If Capture State is OCT Measurement State, then processing goes to Step S807.

In Step S807, this exemplary embodiment of the Imaging apparatus performs processing done during OCT Measurement State. In OCT Measurement State, Control Unit 1045 sends command to the imaging apparatus 100 to continuously scan an area of the fundus of the subject eye, and obtain a set of OCT Tomograms. When the imaging apparatus 100 finishes capturing the OCT tomograms, then the control unit 1045 changes Capture State to Anterior Alignment State.

In OCT Measurement State, Display control unit 1041 does not allow Adjustment of position of Optical head 101, the adjustment of focus of fundus image and adjustment of reference mirror position and adjustment of scanning position of OCT tomogram, as previously explained. In another exemplary embodiment, the Control Unit 1045 sends commands to the OCT Scanner driver to change the scanning position of OCT tomogram to compensate movements of the fundus of the subject eye.

In OCT Measurement State, a Preview Stop icon is disabled, and Measurement Start icon 511 is changed to Measurement Stop icon (not illustrated). If the interpretation unit 1042 detects that Measurement Stop icon was left clicked with the mouse, then the control unit 1045 changes Capture State to Anterior Alignment state, and the control unit 1045 sends a command to imaging apparatus 100 for aborting the capture of OCT Tomograms.

In another exemplary embodiment of the Image Apparatus, in Step S805, if the click detection unit 1042 detects that user has right clicked the mouse when the cursor is over the GUI 500, the control unit 1045 changes Capture State to Anterior Alignment state, and the control unit 1045 sends a command to the imaging apparatus 100 to abort the capture of OCT Tomograms.

In Step S808, the control unit 1045 checks if Capture State is End State. The control unit 1045 sets Capture State to End State when, in any other Capture State, the interpretation unit 1042 detects a left click over a END CG icon 508. If Capture State is END State, then processing flow of this exemplary embodiment of the Imaging Apparatus is finished. If Capture State is different than END State, the display control unit 1045 may show a message or notifies an error.

In another exemplary embodiment of the Imaging Apparatus, a mouse with a single button is used, and a left click done by a mouse with two buttons can be replaced by a single click, and a right click can be replaced by a double click. In another exemplary embodiment of the Imaging Apparatus, keys in the keyboard can also be used instead of the left/right click of a mouse with two buttons.

Figure 9:
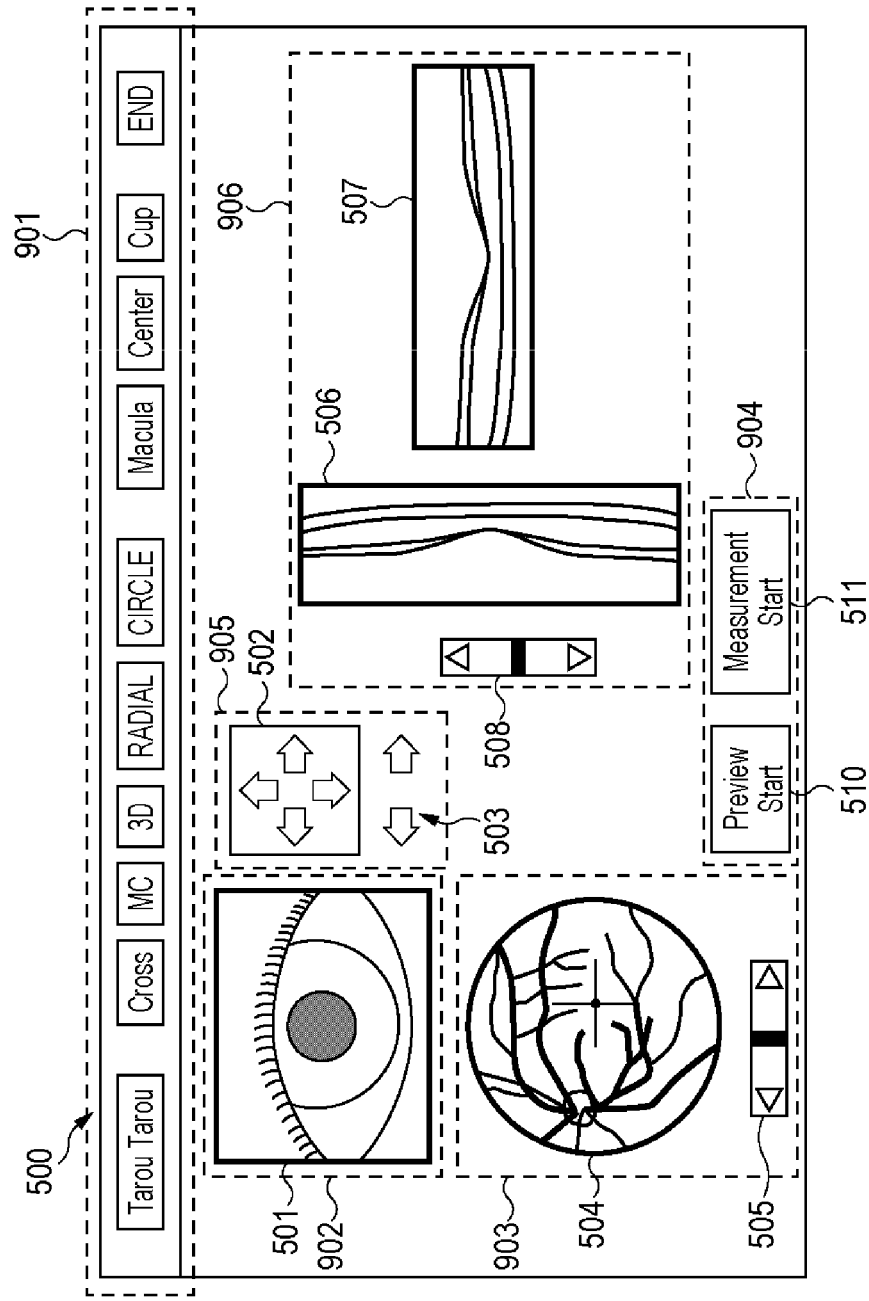
FIG. 9 is a view of the GUI displayed in the Display Unit, according to another exemplary embodiment.

Referring to FIG. 9, another embodiment of the present invention is described below. In the above exemplary embodiment, the processing done after the right click of the mouse is detected, changes accordingly to the state of the Capture State. According to this exemplary embodiment, it is not necessary for the user to move the cursor to icons to change the Capture State. The user is able to change very fast to the next Capture State right after doing adjustment of anterior alignment, focus or coherence gate, by simply clicking the right button of the mouse.

In the above exemplary embodiment, user can change Capture State very fast, but the user can also mistake the use of the right click, and change Capture State when he/she does not want. In this another exemplary embodiment, Display control unit 1041 defines some areas in the GUI 500 where the right click of the mouse can be used, or cannot be used.

The functional block diagram for the exemplary embodiment is the substantially the same as for the first exemplary embodiment, so the explanation will be omitted. In this exemplary embodiment, the control unit 1045 does not recognize right click of the mouse in the regions of the GUI where left click are recognized, when the cursor is over, for example, the anterior image 501, the fundus image 504, the vertical tomogram image 506 or the horizontal tomogram image 507, the XY stage icons 502, Z stage icon 503 and etc. In other words, the control unit 1045 does not perform change on the Capture State in the above conditions.

In another exemplary embodiment, Display control unit 1041 defines some larger areas in the GUI 500 where the right click of the mouse can be used, or cannot be used. With reference to FIG. 9, in this another exemplary embodiment, the control unit 1045 does not recognize right click of the mouse when the cursor is in the regions of the GUI 500 that are inside areas delimited by the intermittent lines, like the areas 901 to 906. In other words, the control unit 1045 does not perform change on the Capture State when the cursor is inside areas delimited by the intermittent lines.

In the exemplary embodiment, the processing done after the right click of the mouse is detected changes accordingly to the state of the Capture State, but there areas in the GUI where the right click is not accepted if the cursor is inside these areas, to reduce the chances of the user to change the state of Capture State without intention.

Figure 10:
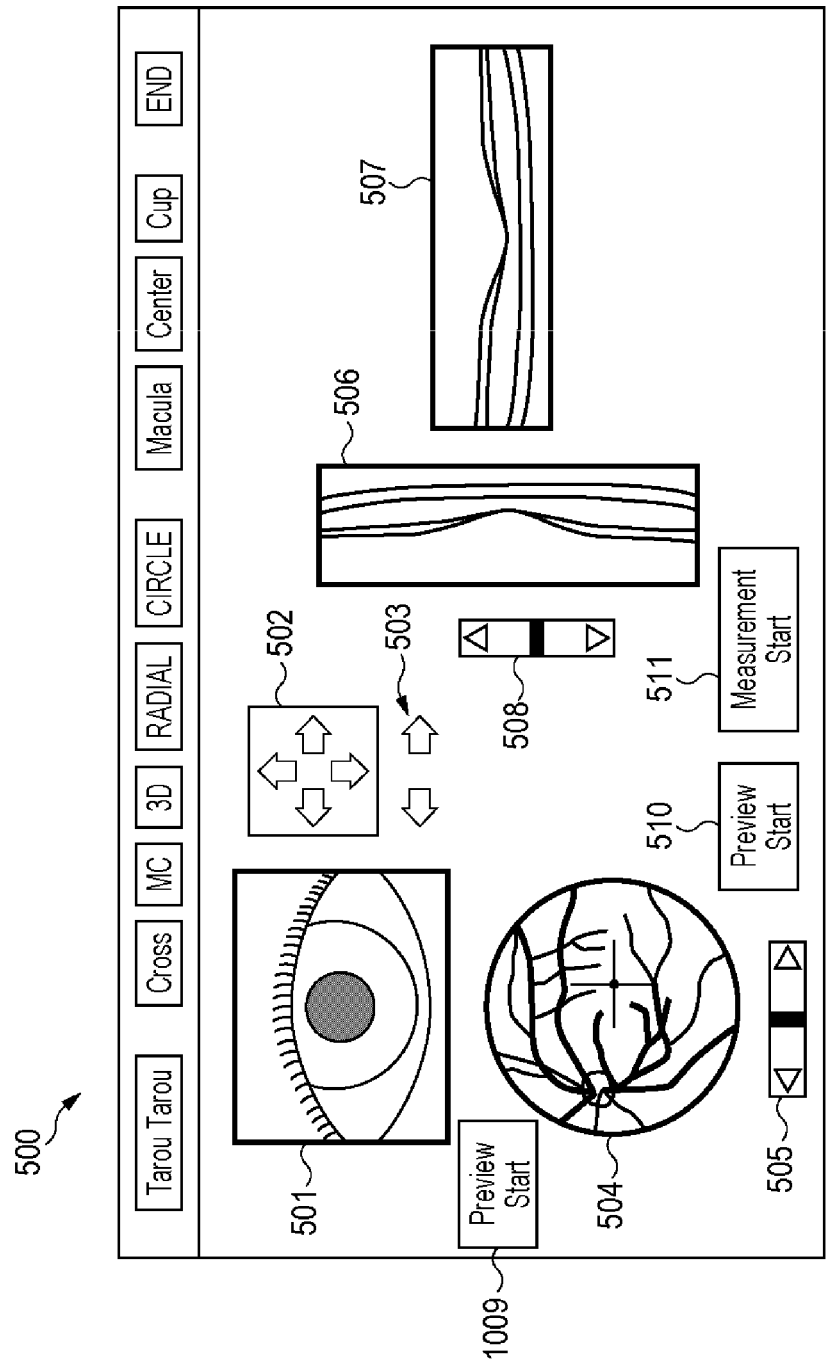
FIG. 10 is a view of the GUI displayed in the Display Unit, according to still another exemplary embodiment.

Referring to FIG. 10, still another embodiment of the present invention is described below. In the above previous exemplary embodiment, user can change Capture State very fast, but the user need use left and right buttons of the mouse, or the user need perform correspondent single click or double click with the mouse. In another exemplary embodiment, Display control unit 1041 adds a pop-up icon close to the areas where mouse can be used for adjustment of the OCT capture.

The functional block diagram for the exemplary embodiment is the same as for the first exemplary embodiment, so the explanation will be omitted. With reference to the GUI 500 shown in FIG. 10, in this exemplary embodiment, Display control unit 1041 adds a pop-up icon close to the areas where left click of the mouse can be used. For example, if cursor is over anterior image 501, a pop-up icon 1009 is shown, in a close position to the anterior image 501. In another exemplary embodiment, the pop-up icon 1009 can be shown inside the anterior image 501. The interpretation unit 1042 detects if the mouse was clicked while the cursor is over the pop-up icon 1009. If the interpretation unit 1042 detects this mouse click, then the control unit 1045 changes the Capture State to the next state, and also changes the functionality of the pop-up icon. In the above exemplary embodiment, the same mouse button can be used for adjusting the capture of OCT tomograms and also for changing the state of the Capture State.

Figure 11:
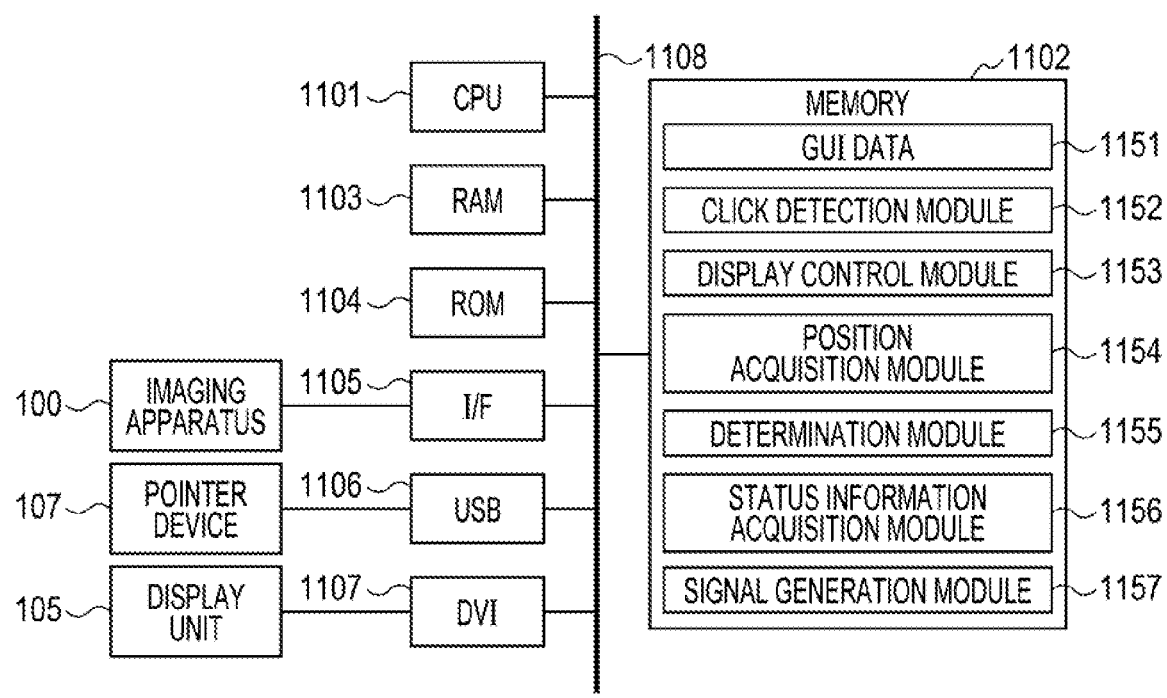
FIG. 11 is a block diagram illustrating hardware of the interactive control apparatus and software modules stored in a memory, in accordance with an exemplary embodiment.

Referring to FIG. 11, yet still another embodiment of the present invention is described. In the embodiment, the interactive control apparatus 104 may also be realized by a computer of a system or apparatus (or devices such as a CPU or MPU) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above-described embodiment(s).

The interactive control apparatus of the embodiment includes a central processing unit (CPU) 1101, a memory, random access memory (RAM) 1103, read only memory 1104, an interface unit (I/F) 1105 for communication with the imaging apparatus 100, a universal serial bus port or a PS/2 port for connecting with the pointer device 107, and the digital video interface 1107 for connecting with the display unit 105, all connected by an internal bus 1108.

The memory 1102 may store GUI data 1151 including GUI image data and GUI position data. The memory may also store software program modules to realize the embodiment of the present invention, as described above. The memory may also store a click detection module 1152, a display control module 1153, a position acquisition module 1154, a determination module 1155, a status information acquisition module 1156, and a signal generation module for controlling the imaging apparatus 100.

The modules are read out and executed by the CPU 1101 to perform the process of the embodiments, for example the process shown in FIGS. 7 and 8. The modules from 1152 to 1157, may function as the unit 1042, 1041, 1043 and 205, 204, 1044, and 1045, respectively, as described with reference to FIG. 2.

The interface unit (I/F) 1105 may include two wired camera-link interface units for transmitting the captured images to the interactive control apparatus, a universal serial bus port for transmitting the control signals from the interactive control apparatus and the preparation status signals from the imaging apparatus. The I/F 1105 may also include an interface unit for transmitting signals for synchronous serial communication of transmitting and receiving multiple frame of images. For this purpose, the program is provided to the computer for example via a network or from a recording medium of various types serving as the memory device (e.g., computer-readable medium).

According to the above described embodiments of the present invention, the specific action can be started in response to the second instruction signal from the pointer device, based on the preparation status of the imaging apparatus.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-190001, filed Aug. 30, 2012, which is hereby incorporated by reference herein in its entirety.

What is claimed is:

1. An interactive control apparatus to be connected with a pointer device, configured to output two instruction signals, and for controlling an optical coherence tomography (OCT) imaging apparatus, wherein the interactive control apparatus is configured to be in one of a plurality of capture states for imaging a subject, the interactive control apparatus comprising:

a processor configured to control the following units:

a display control unit configured to control to display, on a display unit, a graphical user interface having icons to be selected by a virtual pointer controlled by the pointer device, wherein the icons include a specific icon and other icons, wherein the specific icon is assigned to an instruction for changing a current capture state to a next capture state, and each of the other icons is assigned to adjustment of one of a plurality of elements of the OCT imaging apparatus, and wherein selectable icons are different depending on the current capture state of the interactive control apparatus, a detection unit configured to detect a first instruction signal of the pointer device for selecting an icon under the virtual pointer, and to detect a second instruction signal of the pointer device, a check unit configured to check the current capture state of the interactive control apparatus, wherein the current capture state includes at least an alignment state and a preview state, wherein the alignment state is a state in which a position of an optical head of the OCT imaging apparatus is adjustable, and the preview state is a state in which a focus of measurement light and a position of a coherence gate of the OCT imaging apparatus are adjustable, and a control unit configured to control to (a) instruct, in response to the detection of the first instruction signal, the OCT imaging apparatus to perform a first adjustment of a first element, among the plurality of elements, of the OCT imaging apparatus according to the icon selected by the virtual pointer, and to (b) change, in response to the detection of the second instruction signal regardless of a position of the virtual pointer, the current capture state to the preview state in a case where the current capture state is the alignment state, and start the imaging of the subject in a case where the current capture state is the preview state.

2. The interactive control apparatus of claim 1, further comprising a memory unit configured to store a preparation status that indicates an adjustment status of each of the plurality of elements of the OCT imaging apparatus, wherein, in response to the second instruction signal of the pointer device, the control unit is configured to control to instruct to perform a second adjustment of a second element, among the plurality of elements, of the OCT imaging apparatus, of which adjustment is not completed, based on the stored preparation status.

3. The interactive control apparatus of claim 2, wherein the memory unit is configured to store an order to adjust the plurality of elements of the OCT imaging apparatus for performing imaging of a subject, wherein, in a case where the second instruction signal is outputted from the pointer device, the control unit is configured to control to instruct to perform adjustment of the plurality of elements sequentially in the stored order.

4. The interactive control apparatus of claim 2, wherein, in a case where the check unit checks the preparation status indicating completion of the adjustment of the plurality of elements in the preview state, the control unit is configured to control to instruct a start of OCT imaging to the OCT imaging apparatus.

5. The interactive control apparatus of claim 1, wherein the display control unit is configured to control to display, on the display unit, a first graphical user interface for instructing a manual adjustment of each of the plurality of elements selected by the virtual pointer, and a second graphical user interface for instructing an automatic adjustment of each of the plurality of elements selected by the virtual pointer, and wherein the control unit is configured to control to:
instruct, in response to the first instruction signal, the manual adjustment according to the first graphical user interface selected by the virtual pointer,
instruct, in response to the first instruction signal, the automatic adjustment according to the second graphical user interface selected by the virtual pointer, or
instruct the automatic adjustment, in response to the second instruction signal regardless of the position of the virtual pointer, according to an adjustment status of each of the plurality of elements selected by the virtual pointer when the second instruction signal is detected.

6. The interactive control apparatus of claim 1,
wherein the pointer device includes a first button and a second button, and
wherein the detection unit is configured to detect a click of the first button for selecting the icons on the graphical user interface, and to detect a click of the second button regardless of the position of the virtual pointer.

7. The interactive control apparatus of claim 2, wherein, in response to the detection of the second instruction signal regardless of the position of the virtual pointer and as the second adjustment, the control unit is configured to control to instruct to perform at least one of the following: a process for moving an optical head of the OCT imaging apparatus, a process for moving a focus lens of the OCT imaging apparatus, and a process for moving a reference mirror of the OCT imaging apparatus.

8. The interactive control apparatus according to claim 1, further comprising a memory unit configured to store a preparation status that is configured to indicate an adjustment state of each one of the plurality of elements of the OCT imaging apparatus,
wherein each display form of the icons is different based on the preparation status.

9. The interactive control apparatus according to claim 8, wherein the difference in display form of a status icon indicates whether the status icon is available.

10. The interactive control apparatus according to claim 8, wherein the adjustment of an element includes at least one of the following: an adjustment of a stage unit, an adjustment of a focus lens position, and an adjustment of a coherence gate position.

11. The interactive control apparatus according to claim 1,
wherein the icon under the virtual pointer includes a preview start icon,
wherein (a) in a case where the preview start icon is selected by the virtual pointer and the first instruction signal is detected or (b) in a case where the second instruction signal is detected regardless of the position of the virtual pointer, the control unit controls to change the current capture state to an adjustment preview state in which an adjustment of focus lens, an adjustment of coherence gate position, and an adjustment of position of a tomographic image are allowed.

12. The interactive control apparatus according to claim 1, wherein the icon under the virtual pointer includes a measurement start icon,
wherein (a) in a case where the measurement start icon is selected by the virtual pointer and the first instruction signal is detected or (b) in a case where the second instruction signal is detected regardless of the position of the virtual pointer, the control unit controls to change the current capture state to a measurement state in which an tomographic image is obtainable.

13. The interactive control apparatus according to claim 1, wherein the capture state includes Anterior Alignment State, OCT Preview State, and OCT Measurement State,
wherein processing that the OCT imaging apparatus is able to perform in the Anterior Alignment State, in the OCT Preview State, and in the OCT Measurement State is different from one another.

14. An imaging system comprising:
an optical coherence tomography imaging apparatus; and
the interactive control apparatus of claim 1.

15. An interactive control method for controlling an interactive control apparatus to be connected with a pointer device, configured to output two instruction signals, and for controlling an optical coherence tomography (OCT) imaging apparatus, wherein the interactive control apparatus is configured to be in one of a plurality of capture states for imaging a subject, wherein the interactive control apparatus includes a detection unit configured to detect a first instruction signal of the pointer device for selecting an icon under the virtual pointer, and to detect a second instruction signal of the pointer device, the method comprising:

controlling to display, on a display unit, a graphical user interface having icons to be selected by a virtual pointer controlled by the pointer device, wherein the icons include a specific icon and other icons, wherein the specific icon is assigned to an instruction for changing a current capture state to a next capture state, and each of the other icons is assigned to adjustment of one of a plurality of elements of the OCT imaging apparatus, and wherein selectable icons are different depending on the current capture state of the interactive control apparatus;

checking the current capture state of the interactive control apparatus, wherein the current capture state includes at least an alignment state and a preview state, wherein the alignment state is a state in which a position of an optical head of the OCT imaging apparatus is adjustable, and the preview state is a state in which a focus of measurement light and a position of a coherence gate of the OCT imaging apparatus are adjustable; and controlling to (a) instruct, in response to the detection of the first instruction signal, the OCT imaging apparatus to perform a first adjustment of a first element, among the plurality of elements, of the OCT imaging apparatus according to the icon selected by the virtual pointer, and to (b) change, in response to the detection of the second instruction signal regardless of a position of the virtual pointer, the current capture state to the preview state in a case where the current capture state is the alignment state, and start the imaging of the subject in a case where the current capture state is the preview state.

16. A non-transitory computer-readable storage medium storing a program causing a computer to perform the interactive control method of claim 15.

17. An optical coherence tomography (OCT) imaging apparatus for acquiring a tomographic image of a subject, the OCT imaging apparatus comprising:

a processor configured to control the following units:

a display control unit configured to control to display, on a display unit, a graphical user interface having icons to be selected by a virtual pointer controlled by a user input device, wherein the icons include a specific icon and other icons, wherein the specific icon is assigned to an instruction for changing a current capture state to a next capture state, wherein the current capture state includes at least an alignment state and a preview state, wherein the alignment state is a state in which a position of an optical head of the OCT imaging apparatus is adjustable, and the preview state is a state in which a focus of measurement light and a position of a coherence gate of the OCT imaging apparatus are adjustable, a detection unit configured to detect a first instruction signal of the user input device for selecting an icon from the displayed other icons, and to detect a second instruction signal of the user input device, a memory unit configured to store a current capture state of a plurality of capture states for imaging, and a control unit configured to control to (a) instruct, in response to the detection of the first instruction signal, the OCT imaging apparatus to perform a first action according to the icon selected by the virtual pointer, and to (b) change, in response to the detection of the second instruction signal regardless of a position of the virtual pointer, the current capture state to the preview state in a case where the current capture state is the alignment state, and start the imaging of the subject in a case where the current capture state is the preview state.

18. The OCT imaging apparatus of claim 17, wherein the user input device includes a mouse having a first button and a second button, and wherein the detection unit is configured to detect a click of the first button for selecting the icons on the graphical user interface, and to detect a click of the second button regardless of the position of the virtual pointer.

19. The OCT imaging apparatus of claim 17, wherein, in response to the detection of the second instruction signal regardless of the position of the virtual pointer, the control unit is configured to control to instruct at least one of the following: an alignment process, an auto focus process, and a coherence gate positioning process, as a second action.

* * * * *